US009136421B2

(12) United States Patent
Moon et al.

(10) Patent No.: US 9,136,421 B2
(45) Date of Patent: Sep. 15, 2015

(54) WIDE AREA ARRAY TYPE PHOTONIC CRYSTAL PHOTOMIXER FOR GENERATING AND DETECTING BROADBAND TERAHERTZ WAVE

(71) Applicant: Electronics and Telecommunications Research Institute, Daejeon (KR)

(72) Inventors: Kiwon Moon, Gyeongsangbuk-do (KR); Han-Cheol Ryu, Daejeon (KR); Sang-Pil Han, Daejeon (KR); Kyung Hyun Park, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 0 days.

(21) Appl. No.: 14/154,717

(22) Filed: Jan. 14, 2014

(65) Prior Publication Data
US 2014/0197425 A1  Jul. 17, 2014

(30) Foreign Application Priority Data

Jan. 15, 2013 (KR) .................. 10-2013-0004518
Aug. 29, 2013 (KR) .................. 10-2013-0103230

(51) Int. Cl.
*H01L 31/12* (2006.01)
*H01L 31/0232* (2014.01)
(Continued)

(52) U.S. Cl.
CPC .............. *H01L 31/12* (2013.01); *B82Y 20/00* (2013.01); *H01L 31/02327* (2013.01);
(Continued)

(58) Field of Classification Search
CPC .................................................. G02F 2203/00
See application file for complete search history.

(56) References Cited

U.S. PATENT DOCUMENTS 7,421,171 B2    9/2008  Ibanescu et al.
7,498,593 B2 *  3/2009  Shen et al. ............. 250/504 R
(Continued)

FOREIGN PATENT DOCUMENTS

DE   10-2007-044-839 A1   5/2009
EP         1825530 B1      8/2007
(Continued)

OTHER PUBLICATIONS

Arbabi et al., "A terahertz plasmonic metamaterial structure for near-field sensing applications," Infrared, Millimeter and Terahertz Waves, 2008.*
(Continued)

*Primary Examiner* — Thao X Le
*Assistant Examiner* — Xia L Cross
(74) *Attorney, Agent, or Firm* — Rabin & Berdo, P.C.

(57) ABSTRACT

Provided is a broadband photomixer technology that is a core to generate continuous frequency variable and pulsed terahertz waves. It is possible to enhance light absorptance by applying the transmittance characteristic of a 2D light crystal structure and it is possible to increase the generation efficiency of terahertz waves accordingly. Moreover, it is possible to implement a wide area array type terahertz photomixer by applying an interdigit structure and spatially properly arranging a light crystal structure having various cycles. Accordingly, it is possible to solve difficulty in thermal characteristic and light alignment by mitigating the high light density of a light absorption unit and low photoelectric conversion efficiency is drastically improved. In addition, the radiation pattern of terahertz waves may be electrically controlled through the present invention.

20 Claims, 8 Drawing Sheets

(51) Int. Cl.
*H01L 31/0304* (2006.01)
*H01L 31/18* (2006.01)
*H04B 10/90* (2013.01)
*B82Y 20/00* (2011.01)
*H01L 25/16* (2006.01)
*G01N 21/3581* (2014.01)
*G01N 21/3586* (2014.01)
*G02F 1/01* (2006.01)

(52) U.S. Cl.
CPC ......... *H01L 31/03046* (2013.01); *H01L 31/18* (2013.01); *H04B 10/90* (2013.01); *G01N 21/3581* (2013.01); *G01N 21/3586* (2013.01); *G02F 1/0126* (2013.01); *G02F 2202/12* (2013.01); *G02F 2202/32* (2013.01); *G02F 2203/13* (2013.01); *H01L 25/167* (2013.01)

(56) References Cited

U.S. PATENT DOCUMENTS

| | | |
|---|---|---|
| 8,261,557 B2 | 9/2012 | Barker et al. |
| 2007/0121694 A1 | 5/2007 | Okamoto |
| 2009/0262766 A1 | 10/2009 | Chen et al. |

FOREIGN PATENT DOCUMENTS

| | | |
|---|---|---|
| KR | 10-2011-0056597 A | 5/2011 |
| WO | WO-2007/112925 A1 | 10/2007 |

OTHER PUBLICATIONS

Tanoto et al., "Greatly enhanced continuous-wave terahertz emission by nano-electrodes in a photoconductive photomixer," Nature Photonics 6, 121-126 (2012).*

You et al., "Terahertz plasmonic waveguide based on metal rod arrays for nanofilm sensing," Optics Express, 2014, 22(9): 11340.*

* cited by examiner

WIDE AREA ARRAY TYPE PHOTONIC CRYSTAL PHOTOMIXER FOR GENERATING AND DETECTING BROADBAND TERAHERTZ WAVE

CROSS-REFERENCE TO RELATED APPLICATIONS

This U.S. non-provisional patent application claims priority under 35 U.S.C. §119 of Korean Patent Application Nos. 10-2013-0004518, filed on Jan. 5, 2013, and 10-2013-0103230, filed on Aug. 29, 2013, the entire contents of which are hereby incorporated by reference.

BACKGROUND OF THE INVENTION

The present invention disclosed herein relates to a light emitting and absorbing technology, and more particularly, to a continuous frequency variable and pulsed broadband photomixer technology for generating terahertz waves.

Typically, 0.1 to 10 THz (1 THz: $10^{12}$ Hz) regions in an electromagnetic wave spectrum band are defined as terahertz waves. In particular, there are gyro and resonant frequencies of various molecules in 0.1 to 3 THz regions. Molecular fingerprints are obtained by using non-destructive, non-opening, and non-contact methods by utilizing the terahertz waves and thus it is possible to provide a new future core technology in medical treatment, medicine, agriculture/food, environment measurement, biology, communication, non-destructive instruction, and state-of-the-art material evaluation. Thus, intense competition is progressing in order to develop a related core technology.

The terahertz waves have little impact on a human body because they have very low energy of several meV. Thus, although it is expected that needs fir a terahertz wave processing technology emerging as one of core technologies for realizing a people-oriented ubiquitous society will sharply increase, a technology satisfying real time, portable, low-cost, and broadband issues at the same time has not yet been developed, unfortunately. However, various suggestions on terahertz spectroscopy and image field utilization are being provided due to persistent enhancement in technical skills.

SUMMARY OF THE INVENTION

The present invention provides a photonic crystal photomixer that may increase the generation efficiency of terahertz waves and manufacture a wide area photomixer.

The present invention also provides a wide area array type photonic crystal photomixer for generating and detecting broadband terahertz waves that may electrically control the radiation pattern of the terahertz wave . . . .

Embodiments of the present invention provide photoconductive switches include a first electrode coupled to a first level of voltage; a second electrode coupled to a second level of voltage; and a photonic crystal formed between the first and second electrodes over of the photoconductive layer formed on a substrate, the photonic crystal including a plurality of unit metal cell arrays arranged at preset intervals.

In other embodiments of the present invention, wide area array type photonic crystal photomixers include a sub photomixer array including a plurality of first electrode spaced apart from each other side by side and coupled to a bias voltage; a second electrode arranged between the first electrodes and coupled to a ground level; a first photonic crystal that is formed between the upper one of the first electrodes and the second electrode over the photoconductive layer formed on a substrate and that includes a plurality of first unit metal cell arrays arranged at preset distances; and a second photonic crystal that is formed between the lower one of the first electrodes and the second electrode over the photoconductive layer and that includes a plurality of second unit metal cell arrays arranged at preset distances.

In other embodiments of the present invention, wide area array type photonic crystal photomixers for generating and detecting broadband terahertz waves include a plurality of sub photomixer arrays including a plurality of first electrodes spaced apart from each other side by side and coupled to a plurality of bias voltages respectively; a plurality of second electrodes spaced apart from each other side by side, arranged to face the first electrodes respectively and coupled to a ground level in common; and first and second photonic crystals and that are symmetrically formed around a corresponding one of the second electrodes between the corresponding ones of the first electrodes over a photoconductive layer formed on a substrate, and that include a plurality of first and second unit metal cell arrays arranged at preset distances.

BRIEF DESCRIPTION OF THE DRAWINGS

The accompanying drawings are included to provide a further understanding of the present invention, and are incorporated in and constitute a part of this specification. The drawings illustrate exemplary embodiments of the present invention and, together with the description, serve to explain principles of the present invention. In the drawings.

DETAILED DESCRIPTION OF PREFERRED EMBODIMENTS

Figure 1:
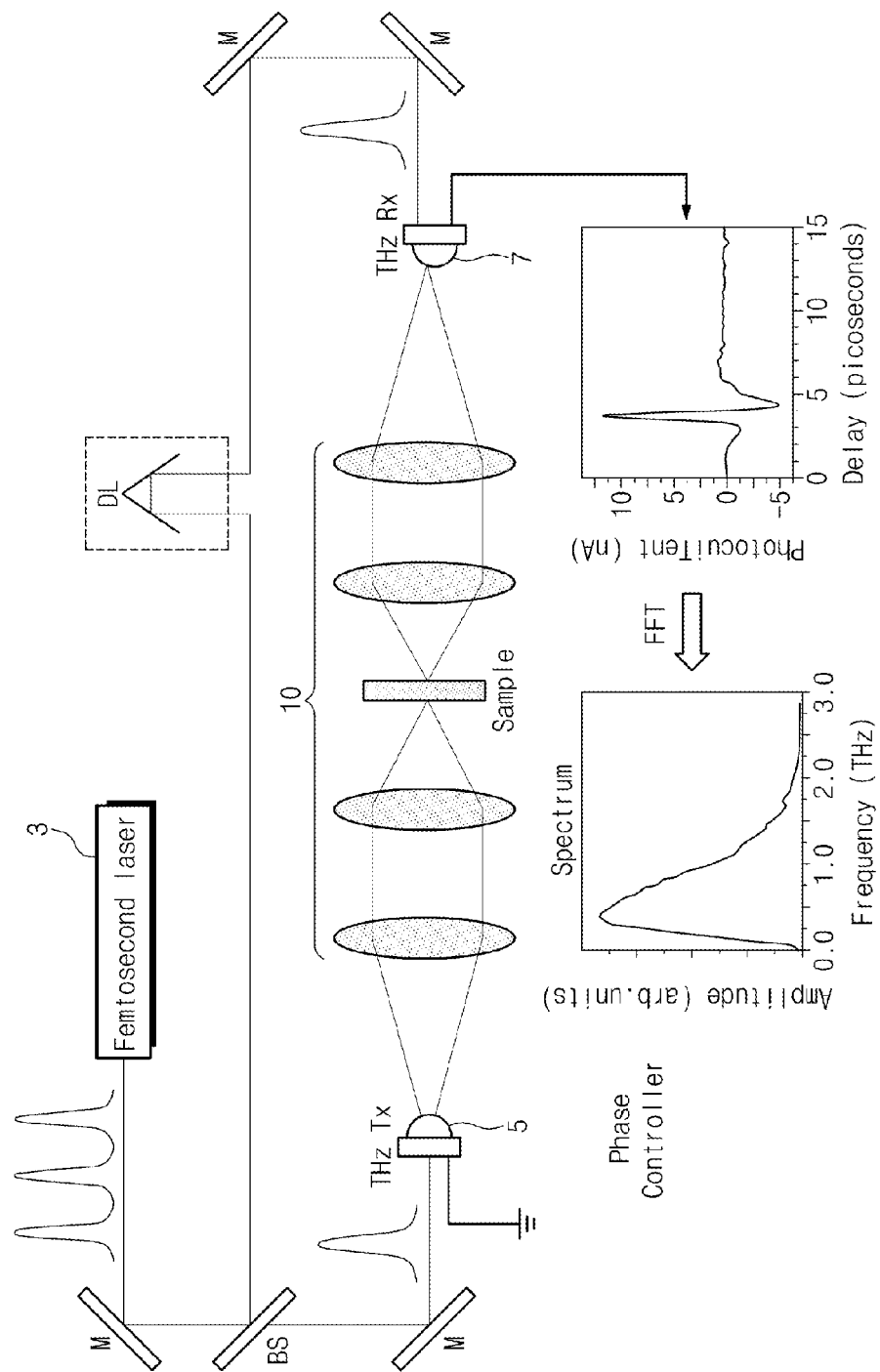
FIG. 1 shows an overview of a typical THz time domain spectroscopy (TDSC) system.

The above-described objects, other objects, characteristics, and advantages of the present invention will be easily understood through the following exemplary embodiments related to the accompanying drawings. However, the present invention is not limited to the following embodiments but may be embodied in other forms. Rather, these embodiments are provided so that this disclosure will be thorough and complete, and will fully convey the scope of the present invention to those skilled in the art.

In the specification, when some elements or lines are referred to as being connected to a target element block, it should be understood that the former can be directly connected to the latter, or indirectly connected to the latter via another element.

Moreover, the same or like reference numerals in each of the drawings represent the same or like components if possible. In some drawings, the connection of elements and lines is just represented to effectively explain technical content and may further include other elements or circuit blocks.

An embodiment described and exemplified herein may include a complementary embodiment thereof, and the details on the basic operation and physical properties of a photomixer will not be provided in order not to make the subject matter of the present invention ambiguous.

Figure 2:
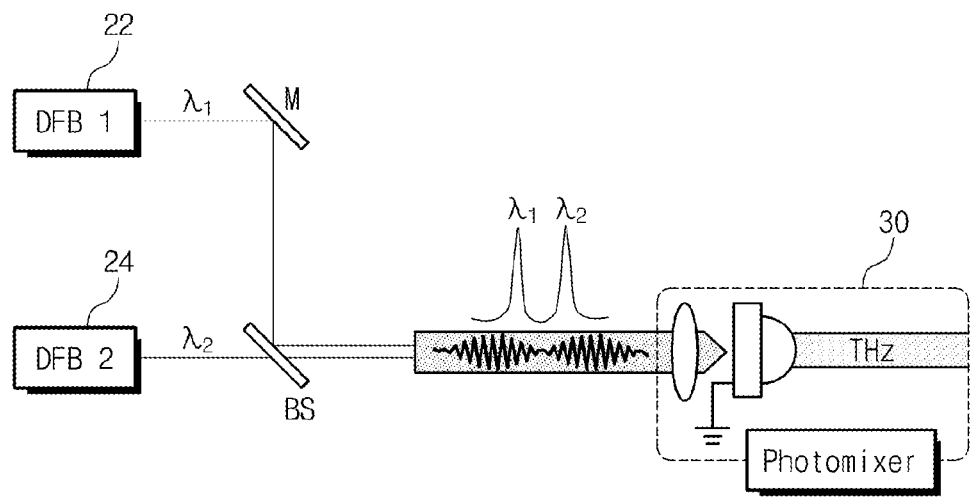
FIG. 2 shows an overview of a typical THz frequency domain spectroscopy (FDS) system generating unit.

FIG. 1 shows an overview of a typical THz time domain spectroscopy (TDSC) system and FIG. 2 shows an overview of a typical THz frequency domain spectroscopy (FDS) system generating unit Unlike a terahertz image field requiring high output power and high sensitivity array type detector selection, a broadband terahertz wave source is a core technology of a system in a terahertz spectroscopy field and is based on a light technology.

A broadband terahertz system most widely used so far is the THz-TDS as shown in FIG. 1. The THz-TDS is a light emitting system that radiates femtosecond-level ultra-short pulse laser beams to semiconductor having an ultra-high response speed to generate terahertz waves.

The THz TDS that is a pulsed broadband terahertz wave generating system as shown in FIG. 1 generally utilizes a Ti: Sapphire laser that is a femtosecond-level ultra-short pulse laser 3. Moreover, a PCA that is a terahertz wave generator due to femtosecond light excitation, namely, an ultra-high frequency optical to electrical converter basically includes a light transmitter 5 and a light receiver 7. The system absorbs a central lasing wavelength of a commercialized Ti: Sapphire laser, 800 nm and a low-temperature growth GaAs thin film having relatively very short carrier lifetime is utilized as a photoconductive antenna (PCA) active material. In a terahertz spectroscopy system configuration, it is necessary to efficiently absorb excitation light or select a material having femtosecond-level carrier lifetime necessary for a broadband characteristic.

A broadband terahertz spectroscopy system including femtosecond-level high output power pulse laser and the PCA is also the first commercialized system because it is relatively easy to provide high SNR and broadband characteristics. However, since the THz-TDS system of FIG. 1 includes a femtosecond-level ultra-short pulse laser 3, a light transmitter 5, a light receiver 7, and an optical system 10 including a light delay unit, it is very expensive. Moreover, the system has a large size due to the optical system 10 that are delicate and complex. Furthermore, because of a light delay consumption time in measuring a time domain signal and a fast Fourier transform (FFT) signal processing time of a measured time domain signal, it is difficult to measure in real time. Thus, such issues are recognized as elements to be solved for the maximization of industrial utilization.

On the other hand, in addition to the THz-TDS system, a pulsed broadband terahertz wave generating technique, many efforts for developing a THz-frequency domain spectroscopy (FDS) generating continuous waves as shown in FIG. 2 are being recently made. The system of FIG. 2 may provide high frequency resolution according to a continuous wave technique and enables low-cost, broadband, and micro-sized system development by utilizing two independent high output power semiconductor lasers 22 and 24. Therefore, since it is possible to develop a terahertz spectroscopy system as a site application type, it is true that related technology development is being competitively made by many organizations. However, particular and actual system application cases are insufficient due to very poor optical to electrical conversion efficiency of a continuous wave technique.

Unlike the pulsed TDS system as shown in FIG. 1, the continuous wave oscillating type FDS system as shown in FIG. 2 is competing with a TDS system. The excitation light source in FIG. 1 is a femtosecond-level ultra-short pulse laser. In contrast, the excitation light in FIG. 2 is emitted by utilizing the beating of two wavelengths that have very stable and high output power.

Except for an excitation light emitting technique, the THz-TDS system of FIG. 1 is similar to the system of FIG. 2 in terms of a terahertz wave generation technique. In the case of PCA, ultra-high frequency optical to electrical converter for the THz-TDS of FIG. 1, it is possible to easily generate broadband terahertz waves by using a several micrometer-sized quadrilateral light excitation region and a very simple dipole antenna due to the high peak value of an ultra-short pulse laser.

On the contrary, in the case of the THz-FDS system of FIG. 2, a terahertz wave having a frequency corresponding to the difference between two wavelengths is generated. Thus, in FIG. 2, the high frequency optical to electrical converter 30 is commonly referred to as a "photomixer" in stead of the term PCA.

In order to develop a photomixer for generating continuous waves, not pulsed waves, several tens of light sources that continuously lase are utilized, unlike a femtosecond laser having a very high peak value. In this case, a finger-shaped interdigitated (IDT) pattern as shown in FIG. 3 is mainly utilized.

The IDT pattern has the drawbacks of easy saturation and depending on the polarization of incident light but it is being actively utilized because it is possible to generate broadband terahertz waves with relatively low input light output power.

Figure 3:
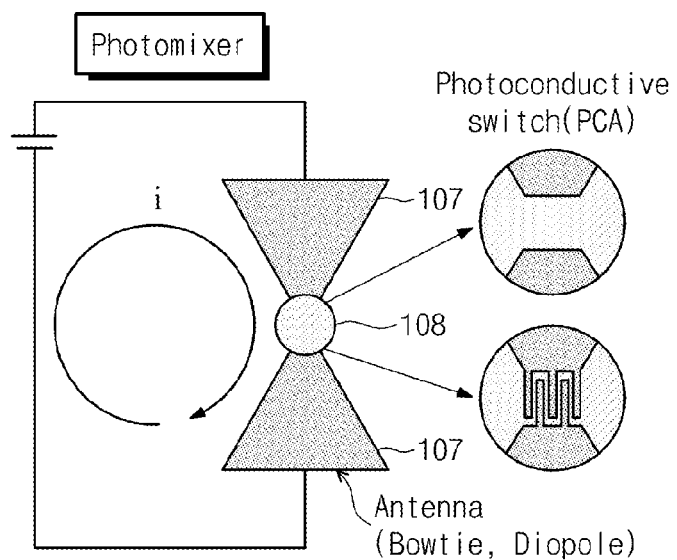
FIG. 3 shows a circuit configuration of a typical photomixer for generating terahertz waves.
Figure 4:
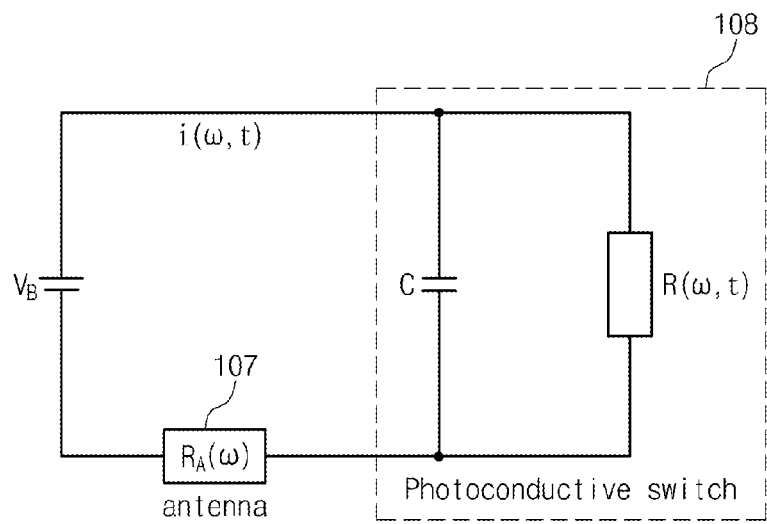
FIG. 4 shows an equivalent circuit of a photomixer for generating terahertz waves of FIG. 3.

FIG. 3 shows a circuit configuration of a typical photomixer for generating terahertz waves. FIG. 4 shows an equivalent circuit of a photomixer for generating terahertz waves of FIG. 3.

A photomixer 30 of FIG. 3 includes a material having a very fast response speed of pico second (10-12). In FIG. 3, the photomixer 30 includes a photoconductive switch (PCS) 108 in which currents flow when light is radiated, and an antenna 107 for securing a gain in one direction of a generated terahertz wave.

The main characteristics of the pulsed broadband terahertz wave generation system or a continuous frequency variable terahertz wave generation system are the characteristic of an excitation light source and the photoelectric efficiency of the PCA or the photomixer that is an optical to electrical converter. Unlike a pulse type, a heat rise effect in a photomixer due to very high input light power needs to be considered when designing a photomixer for generating continuous waves. Main heat sources include material absorption resulting from light injection and Joule heating by currents resulting from photomixer bias application.

If an internal temperature of a photomixer increases, incident light may be early saturated and the internal temperature rises, so a decrease in photoelectric efficiency characteristic may be sharply progressed. Thus, smooth heat emission is necessary for securing high efficiency and in particular, considering heat emission in a continuous wave technique is the most important core issue.

Consider a photomixer for a long wavelength that shows the poorest characteristic among several optical to electrical converters. A continuous frequency variable terahertz wave generation frequency and the difference between two lasing wavelengths of excitation light have the relationship f=cD1/I². The frequency of a terahertz wave is determined by the difference between frequencies $f_1=c/1_1$ and $f_2=c/1_2$ corresponding to lasing wavelengths 11 and 12 of two independent laser beams that are excitation light. In this case, a generated frequency variable terahertz wave source characteristic is directly affected by an excitation light source characteristic. Since all of the stability, line width, polarization, and phase of excitation light affect a generated terahertz wave, many efforts is needed for developing a stable excitation light source.

In order to analyze a terahertz wave output generated through a photomixer, the equivalent circuit as shown in FIG. 4 is frequently utilized. In FIG. 4, main variables that affect photomixer characteristics include an applied voltage $V_B$, the impedance $R_L$ of the antenna 107, photomixer capacitance C, and photomixer photoconductance $G_0$. When an area where light enters Ap, light transmittance T, internal quantum efficiency $h_i$, Planck constant h, charge mobility m, and frequency n are considered and it is assumed that a simple square type photo mixer having no metallic pattern is placed on the area where light enters, the photoconductive $G_0$ is given as the following equation 1.

< Equation 1 >

$$G_0 = \left(\frac{\mu e \tau \eta_i T}{h \nu}\right) \frac{P_o}{A_p} \quad (1)$$

A terahertz wave characteristic output from a photomixer having $G_0$ is given as the following equation. Here, $R_A$ represents radiation resistance of an antenna, C and τ represent the capacitance and carrier extinction time of the photoconductive < Equation 2 >

$$P_{THz}(\omega) = \left(\frac{\frac{1}{2} R_A G_o^2 V_B^2}{(1+(\omega\tau)^2)(1+(\omega R_A C)^2)}\right) \quad (2)$$

In order to generate a high-efficiency terahertz wave, variables that directly affect the photoelectric conversion efficiency of a photomixer along with a high output power light source need to be adjusted.

As could be seen in Equation 2, the photoelectric conversion efficiency is affected by a high response speed of a photomixer, an antenna resistance, and input light intensity. In the case of PCA, pulsed terahertz wave generator, a characteristic decrease due to excitation light is relatively less affected as compared to a continuous wave. However, a photomixer for generating a continuous wave is much affected by junction temperature and temperature increase during activation by continuous input light injection and absorption. The junction temperature Tj is a temperature formed at the interface between air and semiconductor by the Joule heating when applying bias. The junction temperature is an element to be necessarily considered when developing a high-efficiency photomixer, because it determines the maximum value of incident light.

As could be seen in Equations (1) and (2), the characteristic of a broadband photomixer is much affected by a very short carrier extinction time and a photomixer capacitance characteristic. Among others, it is necessary to secure the carrier extinction time that directly affects a broadband characteristic necessary for a terahertz spectrometer.

In order to secure the carrier extinction time, a semiconductor material maintaining a semiconductor monocrystal characteristic and having a very short carrier extinction time is needed. Such a semiconductor material grows generally by using molecular beam epitaxy equipment. The carrier extinction time of general semiconductor is several ns (10-9). Since a time corresponding to 1 THz is 1 ps ($10^{-12}$), the carrier extinction time needs to decrease to 1 ps in order to secure a broadband characteristic. To this end, a semiconductor crystal containing impurities is used.

If a semiconductor crystal grows at a low temperature, impurities are generated because the element of IV group occupies the location of the element of III group in a material. Thus, a femtosecond-level carrier extinction time may secured.

As mentioned above, a GaAs material is being utilized in order to absorb 800 nm light output that is the central lasing wavelength of a Ti: Sapphire laser that is a light source of the THz-TDS system, or an InGaAs material is being mainly used to absorb long wavelength beating light.

In the following, a general photomixer manufacturing method will be compared with a method newly suggested by the present invention.

As could be seen in FIGS. 3 and 4, the photomixer includes the photoconductive switch 108 generating transient currents having a picosecond-level sustain time by reacting with excitation light at a high speed, and the antenna 107 for radiating generated currents in any direction on the space. Various antennas are selected and used according to a use. A broadband antenna is necessarily used for a terahertz spectroscopy system and a high-efficiency resonant antenna is utilized for a terahertz image system.

Figure 5:
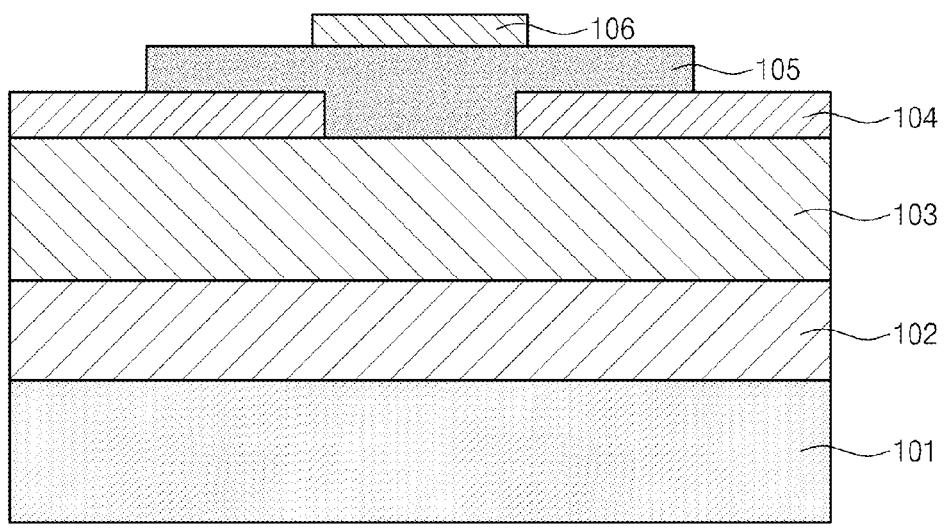
FIG. 5 shows a structure of a flat type photomixer for generating terahertz waves of FIG. 3.

FIG. 5 shows a simplest type photomixer in which only an antenna is manufactured to enable bias application to a material for which a carrier extinction time is secured.

FIG. 5 shows a structure of a flat type photomixer for generating terahertz waves of FIG. 3.

In FIG. 5 representing the sectional structure of a typical flat type photomixer, a reference numeral 101 is a substrate. The substrate 101 may be implemented as a semi-insulating GaAs or InGaAs substrate in order to minimize an amount of terahertz waves that is absorbed by charges on a semiconductor substrate.

A buffer layer 102 is formed on the substrate 101 for normal semiconductor thin film growth. The buffer layer 102 may grow on the substrate 101 by using at least one of AlGaAs, InAlAs, GaAs, and InP materials.

A photoconductive layer that is a core in manufacturing the photomixer is represented by a reference numeral 103. The photoconductive layer 103 may grow through a low temperature technique in order to secure a carrier lifetime.

Semiconductor thin films utilized as active layers needs to utilize a GsAs material of an 800 nm band as a hulk type and a long wavelength area needs to utilize InGaAs, in GaAsP materials of which band gap matches that of an excitation light wavelength. In addition to the bulk type active layer, it is also possible to adopt a multi-layer thin film structure such as InGaAs/InAlAs to easily capture electrons and holes generated by excitation light.

As could be seen in Equation (2), in order to determine to output terahertz waves proportional to the square of an applied voltage and apply bias to the photoconductive switch, forming an electrode by including an antenna is needed.

Subsequently, if an insulating thin film 104, a metallic pattern 105, and a non-reflective film 106 are sequentially formed, a photomixer chip is obtained. Here, the metallic pattern 105 is formed by forming the insulating thin film 104, exposing a portion of the upper part of the photoconductive layer 103 through a photolithography process, and coating a metal film forming the metallic pattern 105.

The non-reflective film 106 is formed to decrease surface reflection due to semiconductor. The non-reflective film 106 is formed only on an area. $A_p$ where light enters through the photolithography process after being coated on the metallic pattern 105.

Figure 6:
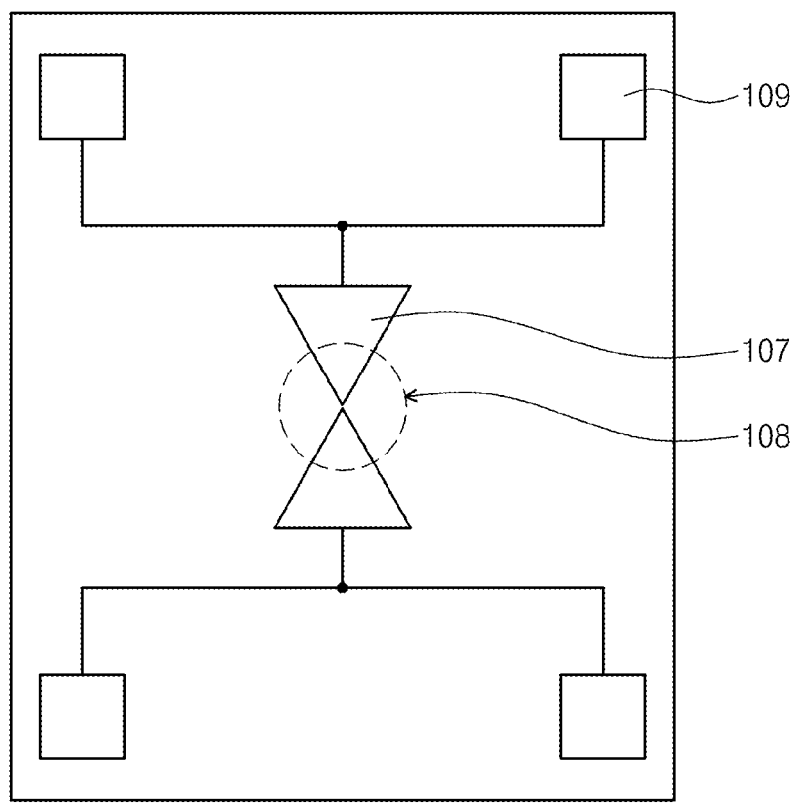
FIG. 6 shows a sectional shape of a photomixer for generating terahertz waves into which an antenna of FIG. 3 is integrated.

FIG. 6 shows a sectional shape of a photomixer for generating terahertz waves into which an antenna of FIG. 3 is integrated.

FIG. 6 is a manufacturing completed picture, a bowtie antenna 107, typical broadband antenna is integrated, and a pad 109 for packaging and a photoconductive switch a broken line part, core of the photomixer are represented.

Incident pulse light or continuous beating light is focused on the active area between the electrodes of the photoconductive switch 108 and the focal diameter of the focused light is about 10 μm corresponding to the distance between the electrodes.

For the typical photomixer as shown in FIG. 6, a decrease in light efficiency resulting from a temperature rise due to high light density on the active area is a drawback to be overcome. Since an additional optical system and high-precision light alignment are needed to focus light, it leads to high cost and low productivity.

In the case of a broadband antenna such ah a bowtie antenna 107 for radiating terahertz waves, the spectrum characteristics of terahertz waves depend on the frequency characteristics of an antenna. The signal amplitude and phase spectrum of the spectrum of a typical broadband antenna are not even. It is one of important conditions that a terahertz photomixer will satisfy, because it is directly connected to the precision of a terahertz spectrometer.

Figure 7:
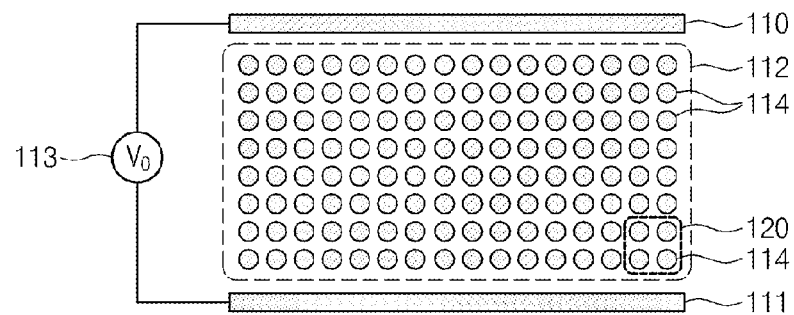
FIG. 7 shows an example of a photonic crystal based photoconductive switch according to an embodiment of the present invention.

Thus, in order to overcome such issues, the photonic crystal based photoconductive switch as shown in FIG. 7 is provided in an embodiment of the present invention.

Figure 8:
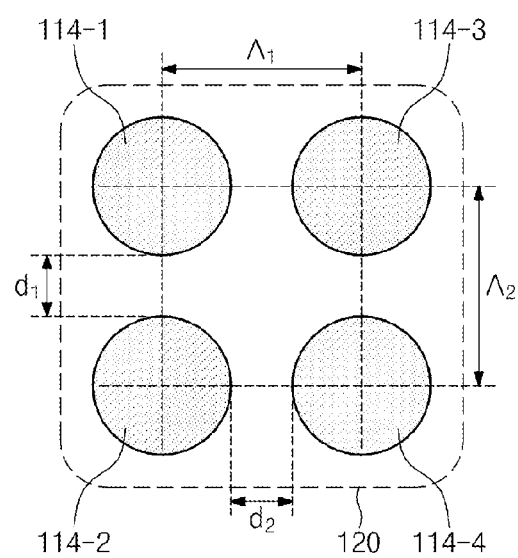
FIG. 8 exemplarily shows a unit metal cell array configuring the photonic crystal of FIG. 7.

FIG. 7 shows an example of a photonic crystal based photoconductive switch according to an embodiment of the present invention. FIG. 8 exemplarily shows a unit metal cell array configuring the photonic crystal of FIG. 7.

Referring to FIG. 7, the photoconductive switch for the photomixer includes a first electrode 110 coupled to a first level of voltage, a second electrode 111 coupled to a second level of voltage, and a photonic crystal 112 that is formed between the first and second electrodes 110 and 111 over of the photoconductive layer formed on a substrate and that includes a plurality of unit metal cell arrays 120 arranged at preset distances.

The unit metal cell array 120 may include at least four metal cells 114 that are arranged at preset distances in first and second (horizontal and vertical) directions.

The sectional shape of the metal cell 114 may be one of a circle, a polygon including a triangle, and a cross.

Here, the preset distance may be formed to make a symmetrical grating structure or an asymmetrical grating structure.

In order to adjust the generation of terahertz waves, it is possible to change the preset distances and arrangement cycle of the plurality of unit metal cell arrays 120 in the design process.

When the first electrode 110 is an anode, the second electrode 111 may be a cathode, and when the second electrode 111 is an anode, the first electrode 110 may be a cathode.

The photoconductive layer may be formed of a GaAs material, an InGaAs material, or an InGaAsP material. Moreover, in some cases, the photoconductive layer may be a multi-layer thin film that includes a layer formed of an InGaAs material and a layer formed of an InAlAs material.

In FIG. 7, the photoconductive switch for the photomixer that includes the anode 110, the cathode 111, and the 2D photonic crystal 112 is electrically controlled by a bias power supply unit V0 113.

The photonic crystal 112 is formed by depositing a metallic thin film having a plane structure on a semiconductor crystal.

The expanded view of the unit metal cell array 120 of the photonic crystal 112 is represented in FIG. 8.

Referring to FIG. 8, the unit metal cell array 120 may include four metal cells 114-1 to 114-4.

It is possible to adjust the absorption degree of light entering the photoconductive layer 103 under the photonic crystal 112 through the adjustment of the cycles $\Lambda_1$ and $\Lambda_2$ and distances $d_1$ and $d_2$ of the photonic crystal. The absorption degree of an incident wave having a specific wavelength into the photoconductive layer 103 is maximized or minimized depending on the cycles and distances of the photonic crystal.

If incident light generates charges on the photoconductive layer 103, instant currents are generated by an applied bias voltage $V_0$, and terahertz waves are generated due to the currents.

If the cycle of the photonic crystal is designed to minimize absorption, the generation of terahertz waves is also minimized, and if the cycle is designed to maximize absorption, the generation of terahertz waves is also maximized.

Although the sectional shape of the metal cell 114 is shown as a circle, the present invention is not limited thereto but may include several shapes such as a triangle, a quadrilateral, and a cross.

A grating structure may also be implemented as a triangle grating structure in addition to the quadrilateral as shown in FIG. 7 and. By differently setting the cycles $\Lambda_1$ and $\Lambda_2$, it is also possible to use an asymmetrical grating structure.

The photonic crystal 112 of FIG. 7 may be entirely configured through the 2D periodic arrangement of the unit metal cell array 120 as shown in FIG. 8.

Figure 9:
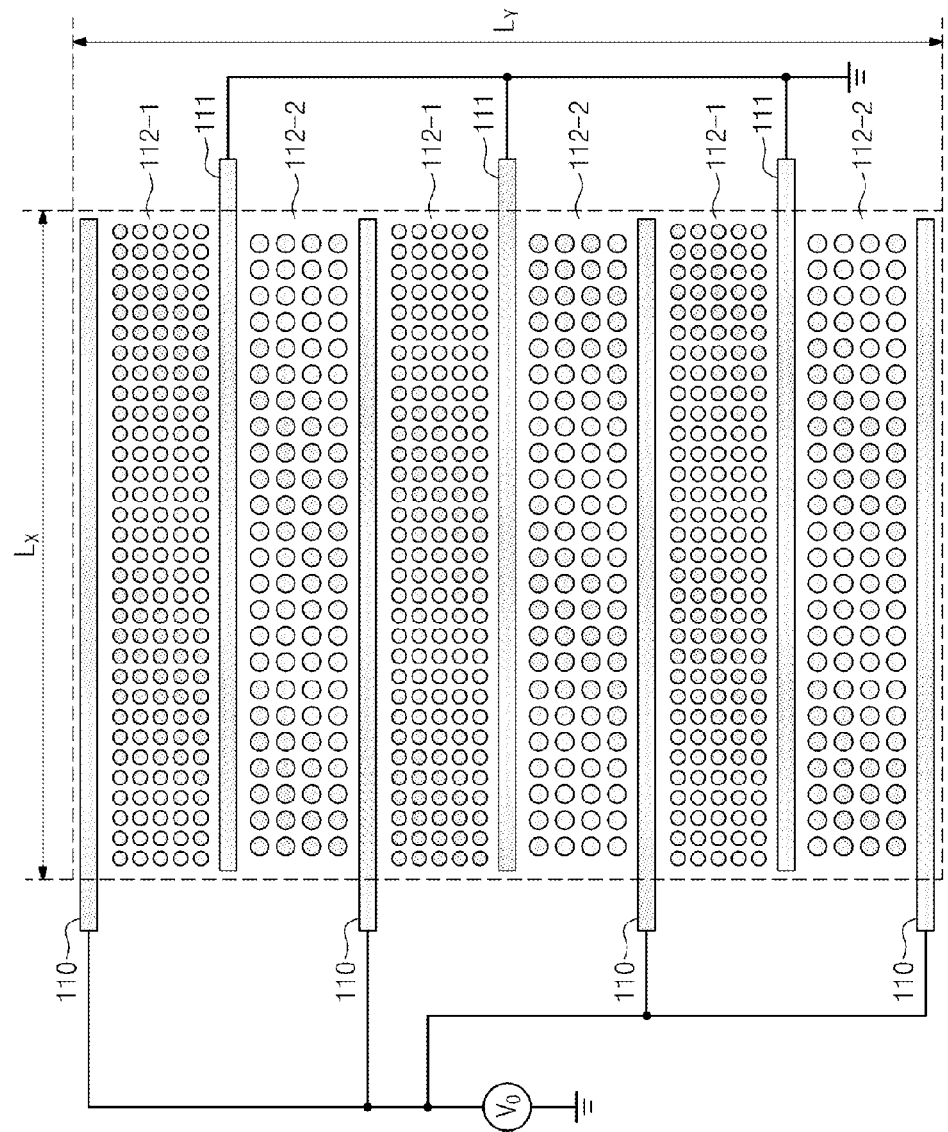
FIG. 9 exemplarily shows a wide area array type photonic crystal photomixer according to another embodiment of the present invention.

FIG. 9 exemplarily shows a wide area array type photonic crystal photomixer according to another embodiment of the present invention.

Figure 10:
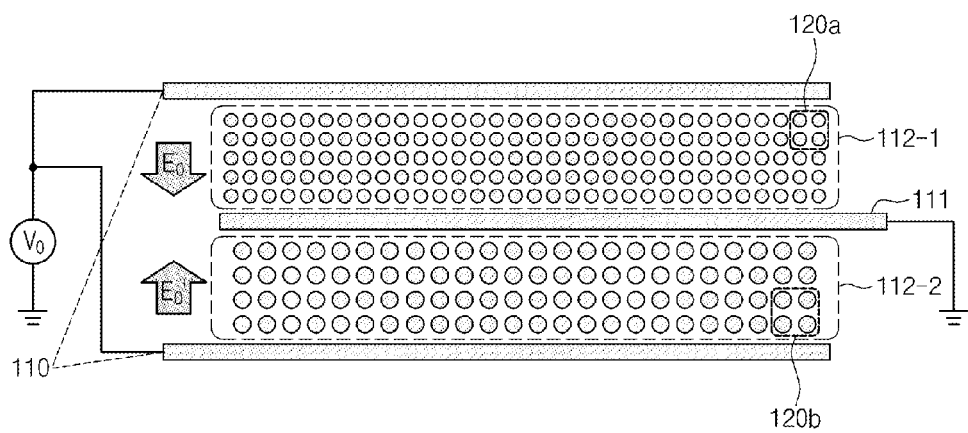
FIG. 10 exemplarily shows a unit structure of the wide area array type photonic crystal photomixer of FIG. 9.

The wide area array type photonic crystal photomixer of FIG. 9 is made by the repetitive arrangement of sub photomixer arrays as shown in FIG. 10.

FIG. 10 exemplarily shows a unit structure of the wide area array type photonic crystal photomixer of FIG. 9.

Firstly, referring to FIG. 10, the sub photomixer array includes a plurality of first electrode 110 spaced apart from each other side by side and coupled to a bias voltage, a second electrode 111 arranged between the first electrodes 110 and coupled to the ground level, a first photonic crystal 112-1 that is formed between the upper one of the first electrodes and the second electrode 111 over the photoconductive layer 103 formed on a substrate and that includes a plurality of first unit metal cell arrays 120a arranged at preset distances, and a second photonic crystal 112-2 that is formed between the lower one of the first electrodes and the second electrode 111 over the photoconductive layer 103 and that includes a plurality of second unit metal cell arrays 120b arranged at preset distances.

The first electrodes 110 functions as an anode in FIG. 10 and the second electrode 111 functions as a cathode.

The first photonic crystal 112-1 works as an absorption (transmittance) area to transmit incident light and the second photonic crystal 112-2 is used as a reflective area designed to reflect incident light.

Turning back to FIG. 9, the horizontal and vertical lengths $L_X$ and $L_Y$ of the wide area array type photonic crystal photomixer are set to be able to maximize the radiation efficiency of terahertz waves. Since a total area is approximately square of several hundred µM, this structure has no need tier focusing light at high precision. Moreover, since in the structure of FIG. 9, the photonic crystal itself also plays the role of radiating terahertz waves, there is no need fir a separate antenna structure.

Referring to FIG. 10, the unit structure of the wide area array type photonic crystal photomixer includes an absorptive area 112-1 and a reflective area 112-2. The absorptive area 112-1 and the reflective area 112-2 may have an IDT structure in which an anode and a cathode cross to implement an array.

Due to the IDT structure, electric fields applied to the absorptive area 112-1 and the reflective area 112-2 have opposite directions as shown in FIG. 10. Thus, if amounts of carriers generated due to light absorption at the absorptive area 112-1 and the reflective area 112-2 are equal, currents flowing from both areas have opposite directions. Thus, because of a cancellation effect resulting therefrom, it is difficult to radiate terahertz waves. In order to solve this drawback, the cycles of the absorptive area 112-1 and the reflective area 112-2 need to be designed to maximize absorption and reflection respectively. As a result, since charges are generated only at the absorptive area 112-1, a forward current flow is maximized, so it is possible to maximize the radiation efficiency of terahertz waves.

Figure 11:
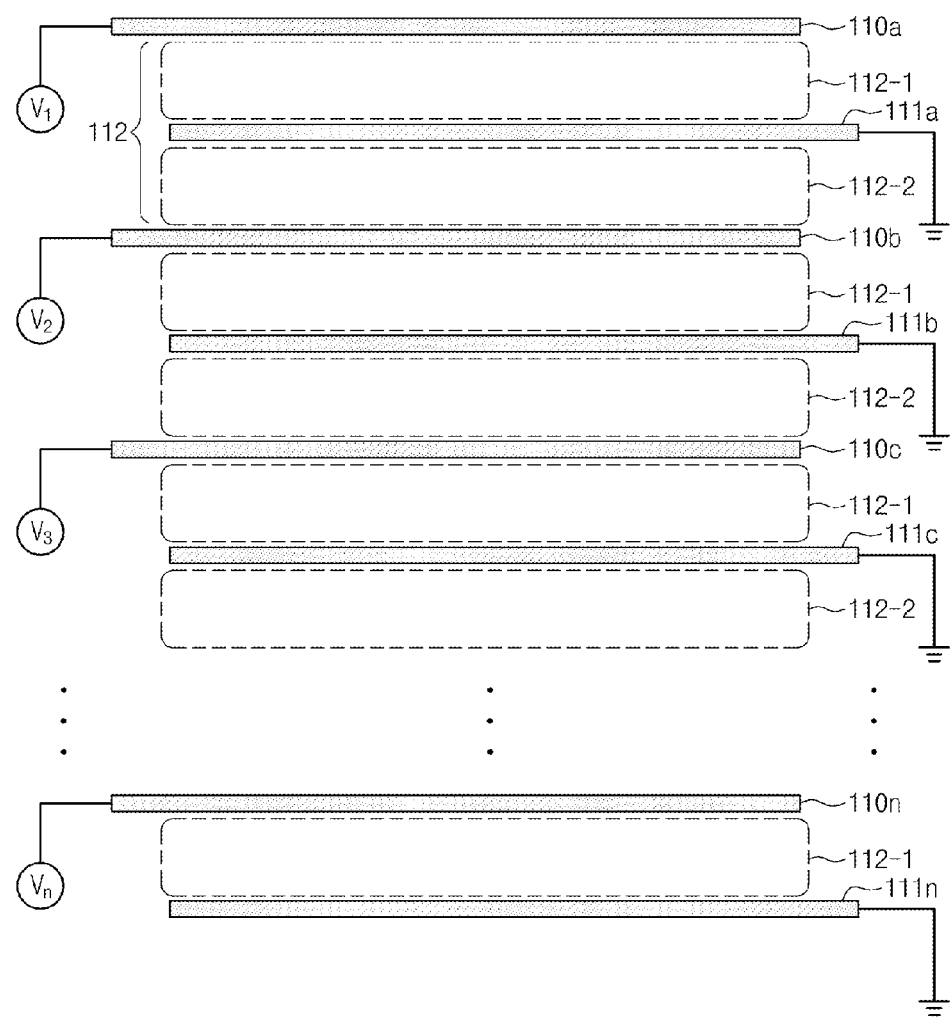
FIG. 11 exemplarily shows a wide area array type photonic crystal photomixer enabling radiation pattern adjustment according to another embodiment of the present invention.

FIG. 11 exemplarily shows a wide area array type photonic crystal photomixer enabling radiation pattern adjustment according to another embodiment of the present invention.

Referring to FIG. 11, the wide area array type photonic crystal photomixer for generating and detecting broadband terahertz waves includes a plurality of sub photomixer arrays 112. The plurality of sub photomixer arrays 112 include a plurality of first electrodes 110a to 110c spaced apart from each other side by side and coupled to a plurality of bias voltages respectively, a plurality of second electrodes 111a to 111e spaced apart from each other side by side, arranged to face the first electrodes 110 respectively and coupled to the ground level in common, and first and second photonic crystals 112-1 and 112-2 that are symmetrically formed around a corresponding one 111a of the second electrodes between the corresponding ones 110a and 110b of the first electrodes over the photoconductive layer 103 formed on a substrate, and that include a plurality of first and second unit metal cell arrays arranged at preset distances.

FIG. 11 is an application technology of the wide area array type photonic crystal photomixer as shown in FIG. 10.

The photomixer is configured to be able to apply different voltages $V_1$ to $V_n$ to anodes 110. Thus, it is possible to spatially control the distribution of currents. Therefore, a radiation pattern may be arbitrarily adjusted by electrical control.

In addition to the arrangement as shown in FIG. 11, a 2D configuration may also vary. It is possible to adjust and modulate any radiation pattern by varying the arrangement.

Hitherto, the best mode was disclosed in the drawings and specification. While specific terms were used, they were not used to limit the meaning or the scope of the present invention described in Claims, but merely used to explain the present invention. Accordingly, a person having ordinary skill in the art will understand from the above that various modifications and other equivalent embodiments are also possible.

For example, in other cases, the details of the photomixer may be differently implemented by changing or adding the structure or configuration of the drawings without departing from the technical spirit of the present invention. Moreover, while the inventive concept is mainly described on handing terahertz waves, the present invention is not limited thereto but may be applied to other electromagnetic waves.

According to the exemplary configurations of the present invention as described above, the generation efficiency of terahertz waves may increase and a wide area array type photomixer may be easily manufactured.

Moreover, the radiation pattern of terahertz waves is electrically controlled.

What is claimed is:

1. A wide area array type photonic crystal photomixer comprising:
   a sub photomixer array comprising:
   a plurality of first electrodes spaced apart from each other side by side and coupled to a bias voltage;
   a single one second electrode arranged between the first electrodes and coupled to a ground level;
   a first photonic crystal that is formed between one of the first electrodes and the one second electrode over a photoconductive layer formed on a substrate, the first photonic crystal including a plurality of first unit metal cell arrays arranged at preset distances from each other, the first unit metal cell arrays being formed so that the first photonic crystal is a light absorption area that transmits incident light; and
   a second photonic crystal that is formed between another of the first electrodes and the one second electrode over the photoconductive layer, the second photonic crystal including a plurality of second unit metal cell arrays arranged at preset distances from each other, the second unit metal cell arrays being formed so that the second photonic crystal is a light reflection area that reflects the incident light.

2. The wide area array type photonic crystal photomixer of claim 1, wherein the first and second unit metal cell arrays each include at least four metal cells that are arranged at preset distances in first and second directions.

3. The wide area array type photonic crystal photomixer of claim 2, wherein each of the metal cells has a sectional shape that is one selected from the group consisting of a circle, a triangle, and a cross.

4. The wide area array type photonic crystal photomixer of claim 1, wherein, the preset distances of each of the first and second unit metal cell arrays are formed to make a symmetrical grating structure or an asymmetrical grating structure.

5. The wide area array type photonic crystal photomixer of claim 1, wherein the preset distances of the first and second unit metal cell arrays and arrangement cycles of the first and second unit metal cell arrays vary to allow generation of terahertz waves to be adjusted.

6. The wide area array type photonic crystal photomixer of claim 1, wherein each of the first electrodes is an anode, and the second electrode is a cathode.

7. The wide area array type photonic crystal photomixer of claim 1, wherein the second electrode is an anode, and each of the first electrodes is a cathode.

8. The wide area array type photonic crystal photomixer of claim 1, wherein the photoconductive layer is formed of a GaAs material.

9. The wide area array type photonic crystal photomixer of claim 1, wherein the photoconductive layer is formed of an InGaAs material or an InGaAsP material.

10. The wide area array type photonic crystal photomixer of claim 1, wherein the photoconductive layer is a multi-layer thin film that includes a layer formed of an InGaAs material and a layer formed of an InAlAs material.

11. The wide area array type photonic crystal photomixer of claim 1, wherein sizes of the first and second unit metal cell arrays are different from each other.

12. The wide area array type photonic crystal photomixer of claim 11, wherein a size of the first unit metal cell arrays is smaller than a size of the second unit metal cell arrays.

13. The wide area array type photonic crystal photomixer of claim 1, wherein a number of the sub photomixer array is three so as to form one large photomixer.

14. The wide area array type photonic crystal photomixer of claim 13, wherein the sub photomixer array has an interdigitated (IDT) structure in which the first and second electrodes are alternately arranged, when forming the one large photomixer.

15. The wide area array type photonic crystal photomixer of claim 1, wherein the photoconductive layer is formed by using a low temperature growth technique.

16. The wide area array type photonic crystal photomixer of claim 1, wherein the preset distances of the first and second unit metal cell arrays and arrangement cycles of the first and second unit metal cell arrays vary to so that the first photonic crystal is the light absorption area and the second photonic crystal is the light reflection area.

17. The wide area array type photonic crystal photomixer of claim 1, wherein the one first electrode, the first photonic crystal, the one second electrode, the second photonic crystal and the another first electrode are disposed in that stated order on a completely straight line.

18. A method of manufacturing a photomixer, the method comprising:
    forming a buffer layer on a substrate;
    forming a photoconductive layer on the buffer layer;
    forming a plurality of first electrodes;
    forming a single one second electrode;
    forming a first photonic crystal between one of the first electrodes and the one second electrode over the photoconductive layer, the first photonic crystal including a plurality of first unit metal cell arrays arranged at preset distances from each other, the first unit metal cell arrays being formed so that the first photonic crystal is a light absorption area that transmits incident light;
    forming a second photonic crystal that is formed between another of the first electrodes and the one second electrode over the photoconductive layer and that includes a plurality of second unit metal cell arrays arranged at preset distances from each other, the second unit metal cell arrays being formed so that the second photonic crystal is a light reflection area that reflects the incident light; and
    electrically controlling light absorptance and light reflectivity on the photoconductive layer by the first and second photonic crystals.

19. The method of claim 18, wherein the preset distances of the first and second unit metal cell arrays and arrangement cycles of the first and second unit metal cell arrays vary to so that the first photonic crystal is the light absorption area and the second photonic crystal is the light reflection area.

20. The method of claim 18, wherein the one first electrode, the first photonic crystal, the one second electrode, the second photonic crystal and the another first electrode are disposed in that stated order on a completely straight line.

* * * * *